(12) United States Patent
Jennings et al.

(10) Patent No.: US 9,682,194 B2
(45) Date of Patent: Jun. 20, 2017

(54) RE-USEABLE AUTO-INJECTOR WITH FILLING MEANS

(75) Inventors: Douglas Ivan Jennings, Royston (GB); Rosemary Louise Burnell, Blinco Grove (GB)

(73) Assignee: Cilag gmBh International, Landas & Gystrasse (CH)

( * ) Notice: Subject to any disclaimer, the term of this patent is extended or adjusted under 35 U.S.C. 154(b) by 443 days.

(21) Appl. No.: 12/997,618

(22) PCT Filed: Jun. 10, 2009

(86) PCT No.: PCT/GB2009/001453
§ 371 (c)(1),
(2), (4) Date: Dec. 13, 2010

(87) PCT Pub. No.: WO2009/153545
PCT Pub. Date: Dec. 23, 2009

(65) Prior Publication Data
US 2011/0130743 A1    Jun. 2, 2011

(30) Foreign Application Priority Data

Jun. 19, 2008 (GB) .................................. 0811345.8

(51) Int. Cl.
*A61M 5/31* (2006.01)
*A61M 5/20* (2006.01)
(Continued)

(52) U.S. Cl.
CPC ............. *A61M 5/20* (2013.01); *A61J 1/2096* (2013.01); *A61M 5/1782* (2013.01);
(Continued)

(58) Field of Classification Search
CPC ................... A61J 1/2089; A61J 1/2096; A61J 2001/2013; A61M 2005/2477;
(Continued)

(56) References Cited

U.S. PATENT DOCUMENTS

| 1,845,036 A | 2/1932 | Busher |
| 2,019,382 A | 10/1935 | Aronson |

(Continued)

FOREIGN PATENT DOCUMENTS

| CH | 518102 A | 1/1972 |
| CN | 2059579 U | 7/1990 |

(Continued)

OTHER PUBLICATIONS

European Search Report dated Aug. 3, 2011; U.S. Appl. No. 11/170,040.
(Continued)

*Primary Examiner* — Matthew F Desanto

(57) ABSTRACT

An injection device having a first sub-assembly comprises a housing and a chamber. The chamber is disposed within the housing and has proximal and distal ends, an inner surface and an exit aperture. The sub-assembly comprises a stopper movably disposed within the chamber. The stopper has an outer surface substantially in contact with the inner surface about its perimeter. The sub-assembly comprises a port adapted to receive a container containing a fluid. The stopper is fixed with respect to the housing and movement of the port causes movement of the exit aperture in relation to the stopper.

10 Claims, 4 Drawing Sheets

(51) Int. Cl.
*A61M 5/178* (2006.01)
*A61M 5/32* (2006.01)
*A61J 1/20* (2006.01)

(52) U.S. Cl.
CPC ............ *A61M 5/2033* (2013.01); *A61J 1/201* (2015.05); *A61M 5/326* (2013.01); *A61M 2005/206* (2013.01); *Y10T 29/49826* (2015.01)

(58) Field of Classification Search
CPC ........... A61M 2005/3125; A61M 2005/31508; A61M 2205/583; A61M 2205/60; A61M 5/1782; A61M 5/20; A61M 5/24; A61M 5/2448; A61M 5/31551; A61M 5/31553; A61M 5/3157
USPC .......................................... 604/506, 200, 207
See application file for complete search history.

(56) References Cited

U.S. PATENT DOCUMENTS

| | | |
|---|---|---|
| 2,147,616 A | 2/1939 | Chaput |
| 2,295,849 A | 9/1942 | Kayden |
| 2,531,267 A | 11/1950 | Harisch |
| 2,764,977 A | 10/1956 | Ferguson |
| 2,828,742 A | 4/1958 | Ashkenaz |
| 2,854,975 A | 10/1958 | Cohen |
| 3,076,455 A | 2/1963 | McConnaughey et al. |
| 3,131,692 A | 5/1964 | Love |
| 3,320,955 A | 5/1967 | Sarnoff |
| 3,329,146 A | 7/1967 | Waldman |
| 3,543,603 A | 12/1970 | Gley |
| 3,656,472 A | 4/1972 | Moura |
| 3,702,608 A | 11/1972 | Tibbs |
| 3,742,948 A | 7/1973 | Post et al. |
| 3,797,488 A | 3/1974 | Hurschman et al. |
| 3,797,489 A | 3/1974 | Sarnoff |
| 3,880,163 A | 4/1975 | Ritterskamp |
| 3,976,069 A | 8/1976 | Ong |
| 4,165,739 A | 8/1979 | Doherty et al. |
| 4,180,070 A | 12/1979 | Genese |
| 4,185,628 A | 1/1980 | Kopfer |
| 4,194,505 A | 3/1980 | Schmitz |
| 4,222,380 A | 9/1980 | Terayama |
| 4,231,368 A | 11/1980 | Becker |
| 4,236,516 A | 12/1980 | Nilson |
| 4,237,882 A | 12/1980 | Wickham |
| 4,299,238 A | 11/1981 | Baidwan et al. |
| 4,333,459 A | 6/1982 | Becker |
| 4,378,015 A | 3/1983 | Wardlaw |
| 4,394,863 A | 7/1983 | Bartner |
| 4,403,989 A | 9/1983 | Christensen et al. |
| 4,407,283 A | 10/1983 | Reynolds |
| 4,425,120 A | 1/1984 | Sampson et al. |
| 4,430,082 A | 2/1984 | Schwabacher |
| 4,521,237 A | 6/1985 | Logothetis |
| 4,561,856 A | 12/1985 | Cochran et al. |
| 4,627,835 A | 12/1986 | Fenton, Jr. |
| 4,636,201 A | 1/1987 | Ambrose et al. |
| 4,639,250 A | 1/1987 | Rycroft |
| 4,642,099 A | 2/1987 | Phillips et al. |
| 4,676,530 A | 6/1987 | Nordgren et al. |
| 4,717,383 A | 1/1988 | Phillips et al. |
| 4,744,786 A | 5/1988 | Hooven et al. |
| 4,787,891 A | 11/1988 | Levin et al. |
| 4,874,383 A | 10/1989 | McNaughton |
| 4,874,384 A | 10/1989 | Nunez |
| 4,929,232 A | 5/1990 | Sweeney et al. |
| 4,969,870 A | 11/1990 | Kramer et al. |
| 4,988,339 A | 1/1991 | Vadher |
| 5,009,646 A | 4/1991 | Sudo et al. |
| 5,026,349 A | 6/1991 | Schmitz et al. |
| 5,057,079 A | 10/1991 | Tiemann et al. |
| 5,092,842 A | 3/1992 | Bechtold et al. |
| 5,098,400 A | 3/1992 | Crouse et al. |
| 5,112,119 A | 5/1992 | Cooke et al. |
| 5,114,406 A | 5/1992 | Gabriel et al. |
| 5,122,119 A | 6/1992 | Lucas |
| 5,137,516 A | 8/1992 | Rand et al. |
| 5,141,496 A | 8/1992 | Dalto et al. |
| 5,147,325 A | 9/1992 | Mitchell et al. |
| 5,156,599 A | 10/1992 | Ranford et al. |
| 5,176,643 A | 1/1993 | Kramer et al. |
| 5,190,526 A | 3/1993 | Murray et al. |
| 5,242,416 A | 9/1993 | Hutson |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,312,364 A | 5/1994 | Jacobs |
| 5,330,081 A | 7/1994 | Davenport |
| 5,330,430 A | 7/1994 | Sullivan |
| 5,356,395 A | 10/1994 | Chen |
| 5,358,489 A | 10/1994 | Wyrick |
| 5,364,369 A | 11/1994 | Reynolds |
| 5,368,577 A | 11/1994 | Teoh et al. |
| 5,372,586 A | 12/1994 | Haber et al. |
| 5,391,151 A | 2/1995 | Wilmot |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,503,627 A | 4/1996 | McKinnon et al. |
| 5,514,097 A | 5/1996 | Knauer |
| 5,520,653 A | 5/1996 | Reilly et al. |
| 5,540,660 A | 7/1996 | Jenson |
| 5,540,666 A | 7/1996 | Barta et al. |
| 5,540,709 A | 7/1996 | Ramel |
| 5,567,160 A | 10/1996 | Massino |
| 5,569,191 A | 10/1996 | Meyer |
| 5,569,192 A | 10/1996 | van der Wal |
| 5,575,777 A | 11/1996 | Cover et al. |
| 5,599,302 A * | 2/1997 | Lilley et al. .................... 604/68 |
| 5,599,309 A | 2/1997 | Marshall et al. |
| 5,607,395 A | 3/1997 | Ragsdale et al. |
| 5,609,577 A | 3/1997 | Haber et al. |
| 5,609,584 A | 3/1997 | Gettig et al. |
| 5,611,785 A | 3/1997 | Mito et al. |
| 5,637,094 A | 6/1997 | Stewart, Jr. et al. |
| 5,645,536 A | 7/1997 | Whisson |
| 5,647,845 A | 7/1997 | Haber et al. |
| 5,649,912 A * | 7/1997 | Peterson ....................... 604/187 |
| 5,658,259 A | 8/1997 | Pearson et al. |
| 5,665,071 A | 9/1997 | Wyrick |
| 5,681,291 A | 10/1997 | Galli |
| 5,697,908 A | 12/1997 | Imbert |
| 5,702,367 A | 12/1997 | Cover et al. |
| 5,704,911 A | 1/1998 | Parsons et al. |
| 5,709,662 A | 1/1998 | Olive et al. |
| 5,713,866 A | 2/1998 | Wilmot |
| 5,748,316 A | 5/1998 | Wakabayashi et al. |
| 5,779,668 A | 7/1998 | Grabenkort |
| 5,779,677 A | 7/1998 | Frezza |
| 5,807,334 A | 9/1998 | Hodosh et al. |
| 5,817,058 A | 10/1998 | Shaw |
| 5,827,262 A | 10/1998 | Neftel et al. |
| 5,843,036 A | 12/1998 | Olive et al. |
| 5,855,839 A | 1/1999 | Brunel |
| 5,865,795 A | 2/1999 | Schiff et al. |
| 5,865,804 A * | 2/1999 | Bachynsky ................... 604/134 |
| 5,868,711 A | 2/1999 | Kramer et al. |
| 5,879,327 A | 3/1999 | Moreau DeFarges et al. |
| 5,913,843 A | 6/1999 | Jentzen |
| 5,928,205 A | 7/1999 | Marshall |
| 5,954,738 A | 9/1999 | LeVaughn et al. |
| 5,957,897 A | 9/1999 | Jeffrey |
| 5,960,797 A | 10/1999 | Kramer et al. |

(56) References Cited

U.S. PATENT DOCUMENTS

| | | |
|---|---|---|
| 5,997,513 A | 12/1999 | Smith et al. |
| 6,007,515 A | 12/1999 | Epstein et al. |
| 6,015,438 A | 1/2000 | Shaw |
| 6,017,330 A | 1/2000 | Hitchins et al. |
| 6,036,675 A | 3/2000 | Thorne et al. |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,070 A | 7/2000 | Hager et al. |
| 6,090,078 A | 7/2000 | Erskine |
| 6,090,897 A | 7/2000 | Akasaki et al. |
| 6,099,503 A | 8/2000 | Stradella |
| 6,099,504 A | 8/2000 | Gross |
| 6,123,684 A * | 9/2000 | Deboer et al. .................. 604/68 |
| 6,139,534 A | 10/2000 | Niedospial, Jr. et al. |
| 6,159,161 A | 12/2000 | Hodosh |
| 6,159,181 A | 12/2000 | Crossman et al. |
| 6,159,184 A | 12/2000 | Perez et al. |
| 6,171,276 B1 | 1/2001 | Adam et al. |
| 6,179,812 B1 | 1/2001 | Botich et al. |
| 6,186,980 B1 | 2/2001 | Brunel |
| 6,190,363 B1 | 2/2001 | Gabbard et al. |
| 6,193,696 B1 | 2/2001 | Jansen et al. |
| 6,203,530 B1 | 3/2001 | Stewart, Sr. |
| 6,209,738 B1 | 4/2001 | Jansen et al. |
| 6,221,044 B1 | 4/2001 | Grecco |
| 6,228,055 B1 | 5/2001 | Foerster et al. |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,290,683 B1 | 9/2001 | Erez et al. |
| 6,293,925 B1 | 9/2001 | Safabash et al. |
| 6,317,939 B1 | 11/2001 | Malin |
| 6,330,960 B1 | 12/2001 | Faughey et al. |
| 6,332,875 B2 | 12/2001 | Inkpen et al. |
| 6,371,939 B2 | 4/2002 | Bergens et al. |
| 6,371,959 B1 | 4/2002 | Trice |
| 6,387,078 B1 | 5/2002 | Gillespie, III |
| 6,391,003 B1 | 5/2002 | Lesch, Jr. |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydion et al. |
| 6,461,333 B1 | 10/2002 | Frezza |
| 6,491,667 B1 | 12/2002 | Keane et al. |
| 6,517,517 B1 | 2/2003 | Farrugia et al. |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Alchas et al. |
| 6,569,124 B1 | 5/2003 | Perouse |
| 6,572,581 B1 | 6/2003 | Landau |
| 6,575,939 B1 | 6/2003 | Brunel |
| 6,585,702 B1 | 7/2003 | Brunel |
| 6,589,210 B1 | 7/2003 | Rolfe |
| 6,595,957 B1 | 7/2003 | Griffiths et al. |
| 6,595,962 B1 | 7/2003 | Perthu |
| 6,599,272 B1 | 7/2003 | Hjertman et al. |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landau |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau et al. |
| 6,692,469 B1 | 2/2004 | Weekes et al. |
| 6,699,220 B2 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard et al. |
| 6,746,429 B2 | 6/2004 | Sadowski et al. |
| 6,746,438 B1 * | 6/2004 | Arnissolle ..................... 604/411 |
| 6,767,336 B1 | 7/2004 | Kaplan |
| 6,770,056 B2 | 8/2004 | Price et al. |
| 6,776,777 B2 | 8/2004 | Barrelle |
| 6,783,509 B1 | 8/2004 | Landau et al. |
| 6,793,161 B1 | 9/2004 | Fujita et al. |
| 6,796,967 B2 | 9/2004 | Jensen |
| 6,811,548 B2 | 11/2004 | Jeffrey |
| 6,817,987 B2 | 11/2004 | Vetter et al. |
| 6,846,303 B2 | 1/2005 | Eakins et al. |
| 6,875,205 B2 | 4/2005 | Leinsing |
| 6,890,319 B1 | 5/2005 | Crocker |
| 6,899,698 B2 | 5/2005 | Sams |
| 6,902,543 B1 | 6/2005 | Cherif-Cheikh et al. |
| 6,932,793 B1 | 8/2005 | Marshall et al. |
| 6,939,319 B1 | 9/2005 | Anstead et al. |
| 6,939,330 B1 | 9/2005 | McConnell et al. |
| 6,979,316 B1 | 12/2005 | Rubin et al. |
| 7,066,907 B2 | 6/2006 | Crossman et al. |
| 7,097,071 B2 | 8/2006 | Anderson et al. |
| 7,097,634 B2 | 8/2006 | Gilbert |
| 7,118,553 B2 | 10/2006 | Scherer |
| 7,156,823 B2 | 1/2007 | Landau et al. |
| 7,160,913 B2 | 1/2007 | Schneider |
| 7,294,122 B2 | 11/2007 | Kubo et al. |
| 7,354,427 B2 | 4/2008 | Fangrow |
| RE40,428 E | 7/2008 | Keane et al. |
| 7,442,185 B2 | 10/2008 | Amark et al. |
| 7,470,258 B2 | 12/2008 | Barker et al. |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,534,238 B2 | 5/2009 | Fangrow |
| 7,547,300 B2 | 6/2009 | Fangrow |
| 7,569,043 B2 | 8/2009 | Fangrow |
| 7,618,396 B2 | 11/2009 | Slate et al. |
| 7,635,356 B2 | 12/2009 | Stamp |
| 7,645,271 B2 | 1/2010 | Fangrow |
| 7,654,995 B2 | 2/2010 | Warren et al. |
| 7,658,733 B2 | 2/2010 | Fangrow |
| 7,678,333 B2 | 3/2010 | Reynolds et al. |
| 7,682,345 B2 | 3/2010 | Savage |
| 7,717,879 B2 | 5/2010 | Mansouri |
| 7,744,561 B2 | 6/2010 | Stamp |
| 7,759,654 B2 | 7/2010 | Yan et al. |
| 7,794,434 B2 | 9/2010 | Mounce et al. |
| 7,799,009 B2 | 9/2010 | Niedospial, Jr. et al. |
| 7,811,262 B2 | 10/2010 | Moberg et al. |
| 7,828,764 B2 | 11/2010 | Moberg et al. |
| 7,871,397 B2 | 1/2011 | Schraga |
| 7,879,010 B2 | 2/2011 | Hunn et al. |
| 7,883,499 B2 | 2/2011 | Fangrow |
| 7,959,715 B2 | 6/2011 | Kavazov et al. |
| 7,972,321 B2 | 7/2011 | Fangrow |
| 7,976,499 B2 | 7/2011 | Grunhut et al. |
| 8,100,154 B2 | 1/2012 | Reynolds et al. |
| 8,177,768 B2 | 5/2012 | Leinsing |
| 8,277,414 B2 | 10/2012 | Barrow-Williams et al. |
| 8,313,463 B2 | 11/2012 | Barrow-Williams et al. |
| 8,409,138 B2 | 4/2013 | James et al. |
| 8,409,141 B2 | 4/2013 | Johansen et al. |
| 8,491,530 B2 | 7/2013 | Maritan |
| 8,696,628 B2 | 4/2014 | Grunhut |
| 8,932,264 B2 | 1/2015 | DeSalvo |
| 9,314,574 B2 | 4/2016 | Roberts et al. |
| 2001/0005781 A1 | 6/2001 | Bergens et al. |
| 2001/0021828 A1 | 9/2001 | Fischer et al. |
| 2001/0037087 A1 | 11/2001 | Knauer |

(56) References Cited

U.S. PATENT DOCUMENTS

| | | |
|---|---|---|
| 2001/0037089 A1 | 11/2001 | Domici, Jr. |
| 2001/0049496 A1 | 12/2001 | Kirchhofer et al. |
| 2001/0051789 A1 | 12/2001 | Parsons |
| 2002/0032412 A1 | 3/2002 | Riemelmoser |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0165500 A1 | 11/2002 | Bechtold et al. |
| 2002/0173752 A1* | 11/2002 | Polzin .................. 604/233 |
| 2002/0183690 A1 | 12/2002 | Arnisolle |
| 2003/0036679 A1 | 2/2003 | Kortenbach |
| 2003/0036725 A1* | 2/2003 | Lavi et al. ............. 604/91 |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1* | 6/2003 | Lavi et al. ............. 604/136 |
| 2003/0109833 A1 | 6/2003 | Sharpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0229308 A1 | 12/2003 | Tsals et al. |
| 2003/0233070 A1 | 12/2003 | De La serna et al. |
| 2003/0236502 A1 | 12/2003 | De La Serna et al. |
| 2003/0236504 A1 | 12/2003 | Chen |
| 2004/0002684 A1 | 1/2004 | Lopez |
| 2004/0015134 A1 | 1/2004 | Lavi et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0094396 A1 | 5/2004 | Lee et al. |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0020980 A1 | 1/2005 | Inoue et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0113747 A1* | 5/2005 | Moir .................. 604/87 |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0168855 A1 | 8/2005 | Fanelli et al. |
| 2005/0203466 A1 | 9/2005 | Hommann et al. |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0267403 A1 | 12/2005 | Landau et al. |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178630 A1 | 8/2006 | Bostrom et al. |
| 2006/0178631 A1 | 8/2006 | Gillespie et al. |
| 2006/0178642 A1 | 8/2006 | Gillespie et al. |
| 2006/0184119 A1 | 8/2006 | Remde et al. |
| 2006/0184137 A1 | 8/2006 | Reynolds |
| 2006/0189938 A1 | 8/2006 | Hommann et al. |
| 2006/0200093 A1 | 9/2006 | Lopez |
| 2006/0206060 A1 | 9/2006 | Lopez |
| 2006/0224124 A1 | 10/2006 | Scherer |
| 2006/0229572 A1 | 10/2006 | Lopez |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0066939 A1 | 3/2007 | Krulevitch et al. |
| 2007/0078382 A1 | 4/2007 | Hommann et al. |
| 2007/0118094 A1 | 5/2007 | Bingham et al. |
| 2007/0142787 A1 | 6/2007 | Scherer |
| 2007/0156091 A1 | 7/2007 | Fathallah et al. |
| 2007/0156112 A1 | 7/2007 | Walsh |
| 2007/0208296 A1 | 9/2007 | Paproski et al. |
| 2008/0033395 A1 | 2/2008 | Alchas |
| 2008/0172024 A1 | 7/2008 | Yow |
| 2008/0213590 A1 | 9/2008 | Greiner et al. |
| 2008/0269680 A1 | 10/2008 | Ibranyan et al. |
| 2008/0306443 A1 | 12/2008 | Neer et al. |
| 2008/0312602 A1 | 12/2008 | Barrow-Williams et al. |
| 2008/0312606 A1 | 12/2008 | Harrison et al. |
| 2009/0036764 A1 | 2/2009 | Rivas et al. |
| 2009/0054849 A1 | 2/2009 | Burnell et al. |
| 2009/0088688 A1 | 4/2009 | Timothy Donald et al. |
| 2009/0209554 A1 | 8/2009 | Boyd et al. |
| 2009/0234297 A1 | 9/2009 | Jennings |
| 2010/0016793 A1 | 1/2010 | Jennings et al. |
| 2010/0036319 A1 | 2/2010 | Drake et al. |
| 2010/0063444 A1 | 3/2010 | Wikner |
| 2011/0092954 A1 | 4/2011 | Jennings |
| 2011/0098647 A1 | 4/2011 | Jennings |
| 2011/0098655 A1 | 4/2011 | Jennings et al. |
| 2011/0130743 A1 | 6/2011 | Jennings et al. |
| 2011/0282278 A1 | 11/2011 | Stamp et al. |
| 2012/0232491 A1 | 9/2012 | Jennings |
| 2012/0323177 A1 | 12/2012 | Adams et al. |
| 2013/0096512 A1 | 4/2013 | Ekman et al. |
| 2013/0267898 A1 | 10/2013 | Hourmand et al. |
| 2013/0317446 A1 | 11/2013 | Hourmand et al. |
| 2013/0331794 A1 | 12/2013 | Ekman et al. |
| 2013/0338601 A1 | 12/2013 | Cowe |

(56) References Cited

U.S. PATENT DOCUMENTS

| | | | |
|---|---|---|---|
| 2013/0345643 A1 | 12/2013 | Hourmand et al. | |
| 2014/0257193 A1 | 9/2014 | Bostrom et al. | |

FOREIGN PATENT DOCUMENTS

| | | |
|---|---|---|
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 1/1997 |
| DE | 19603707 A1 | 8/1997 |
| DE | 69506521 T2 | 6/1999 |
| DE | 10137962 A1 | 2/2003 |
| DE | 10207276 A1 | 9/2003 |
| DE | 20311996 U1 | 10/2003 |
| EP | 0111724 B1 | 11/1983 |
| EP | 0096314 A2 | 12/1983 |
| EP | 0144625 A2 | 6/1985 |
| EP | 0240787 A2 | 3/1987 |
| EP | 0338806 A2 | 10/1989 |
| EP | 0515473 B1 | 12/1992 |
| EP | 0518416 A1 | 12/1992 |
| EP | 0331452 A2 | 8/1993 |
| EP | 0585626 A1 | 3/1994 |
| EP | 0389938 B1 | 5/1994 |
| EP | 0516473 B1 | 2/1996 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |
| EP | 0941133 B1 | 4/2004 |
| EP | 1124601 B1 | 12/2004 |
| EP | 1364667 B1 | 4/2005 |
| EP | 1208858 B1 | 6/2006 |
| EP | 1755710 A1 | 2/2007 |
| EP | 1586341 B1 | 1/2008 |
| EP | 1932558 A1 | 6/2008 |
| EP | 2023980 A1 | 2/2009 |
| EP | 2129414 A1 | 12/2009 |
| EP | 1755706 B1 | 3/2010 |
| EP | 1928523 B1 | 7/2010 |
| EP | 1518575 B1 | 11/2010 |
| EP | 2468330 A1 | 6/2012 |
| EP | 2340863 B1 | 11/2013 |
| EP | 2620174 B1 | 5/2014 |
| EP | 2675509 B1 | 4/2015 |
| EP | 2705861 B1 | 4/2015 |
| EP | 2414003 B1 | 5/2015 |
| EP | 2464401 B1 | 5/2015 |
| EP | 2493531 B1 | 7/2015 |
| EP | 2705862 B1 | 7/2015 |
| EP | 2588173 B1 | 10/2015 |
| EP | 2470241 B1 | 11/2015 |
| EP | 2768556 B1 | 12/2015 |
| EP | 2355872 B1 | 1/2016 |
| EP | 2720738 B1 | 1/2016 |
| EP | 1412000 B1 | 2/2016 |
| EP | 2671606 B1 | 3/2016 |
| EP | 2760507 B1 | 4/2016 |
| FR | 1014881 A | 8/1952 |
| FR | 1169935 A | 1/1959 |
| FR | 1538565 A | 9/1968 |
| FR | 2506161 A1 | 11/1982 |
| FR | 2629706 A | 10/1989 |
| FR | 2665079 A1 | 1/1992 |
| FR | 2717086 A1 | 9/1995 |
| FR | 2741810 A1 | 6/1997 |
| FR | 2805868 A1 | 9/2001 |
| FR | 2830765 A1 | 4/2003 |
| FR | 2861310 A1 | 4/2005 |
| GB | 143084 | 5/1920 |
| GB | 0412054 | 6/1934 |
| GB | 728248 | 4/1955 |
| GB | 909898 | 11/1962 |
| GB | 1263355 | 2/1972 |
| GB | 1311937 A | 3/1973 |
| GB | 1514725 | 6/1978 |
| GB | 2338033 A | 12/1999 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 A | 11/2005 |
| GB | 2414399 A | 11/2005 |
| GB | 2414400 A | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424837 A | 10/2006 |
| GB | 2424838 A | 10/2006 |
| GB | 2425062 A | 10/2006 |
| GB | 2433035 A | 6/2007 |
| GB | 2437922 A | 11/2007 |
| GB | 2438591 A | 12/2007 |
| GB | 2443606 A | 5/2008 |
| GB | 2445090 A | 6/2008 |
| GB | 2446778 A | 8/2008 |
| GB | 2451663 A | 2/2009 |
| GB | 2451665 A | 2/2009 |
| GB | 2452286 A | 3/2009 |
| GB | 2515041 B | 12/2014 |
| JP | 59-115053 A | 7/1984 |
| JP | 2-185261 A | 7/1990 |
| JP | 2-502971 T | 9/1990 |
| JP | H 02-299660 A | 12/1990 |
| JP | 11-501549 T | 2/1992 |
| JP | 5-161712 A | 6/1993 |
| JP | 6-209996 A | 8/1994 |
| JP | 6-508773 T | 10/1994 |
| JP | 6-327770 A | 11/1994 |
| JP | H 07-116224 A | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 A | 8/1998 |
| JP | 11-503637 T | 3/1999 |
| JP | 11-504536 T | 4/1999 |
| JP | 11-164887 T | 6/1999 |
| JP | 11-512332 T | 10/1999 |
| JP | 2000-126293 A | 5/2000 |
| JP | 2000-510021 T | 8/2000 |
| JP | 2001-046498 A | 2/2001 |
| JP | 2001-212237 A | 8/2001 |
| JP | 2002-500933 T | 1/2002 |
| JP | 2002-502296 T | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2002-532161 T | 10/2002 |
| JP | 2003-511105 T | 3/2003 |
| JP | 2003-532500 T | 11/2003 |
| JP | 2003-533288 A | 11/2003 |
| JP | 2004-533282 T | 11/2004 |
| JP | 2004-537376 A | 12/2004 |
| JP | 2005-508214 A | 3/2005 |

(56) References Cited

FOREIGN PATENT DOCUMENTS

| | | |
|---|---|---|
| JP | 2005-177503 A | 7/2005 |
| JP | 2004-33737 A | 8/2005 |
| JP | 2006-223858 A | 8/2006 |
| JP | 2007-207611 A | 8/2007 |
| JP | 2008-284177 A | 11/2008 |
| NZ | 335985 A | 4/2001 |
| NZ | 573171 A | 11/2010 |
| NZ | 573350 A | 12/2010 |
| WO | WO 87/07843 A1 | 12/1987 |
| WO | WO 88/10129 A1 | 12/1988 |
| WO | WO 98/10129 A1 | 12/1988 |
| WO | WO 92/19296 A | 11/1992 |
| WO | WO 93/02186 A1 | 2/1993 |
| WO | WO 93/21986 A2 | 11/1993 |
| WO | WO 93/23098 A1 | 11/1993 |
| WO | WO 94/04207 A1 | 3/1994 |
| WO | WO 94/07554 A1 | 4/1994 |
| WO | WO 94/11041 | 5/1994 |
| WO | WO 94/13342 A1 | 6/1994 |
| WO | WO 94/21316 A1 | 9/1994 |
| WO | WO 94/22511 A1 | 10/1994 |
| WO | WO 95/04562 A1 | 2/1995 |
| WO | WO 95/29720 A1 | 11/1995 |
| WO | WO 95/31235 A1 | 11/1995 |
| WO | WO 95/35126 A1 | 11/1995 |
| WO | WO 95/35126 A1 | 12/1995 |
| WO | WO 96/30065 A1 | 10/1996 |
| WO | WO 97/10865 A1 | 3/1997 |
| WO | WO 97/13538 A1 | 4/1997 |
| WO | WO 97/48430 A1 | 12/1997 |
| WO | WO 98/11927 A1 | 3/1998 |
| WO | WO 99/03529 A2 | 1/1999 |
| WO | WO 99/10030 A2 | 3/1999 |
| WO | WO 99/22789 A1 | 5/1999 |
| WO | WO 99/37343 A | 7/1999 |
| WO | WO 99/53979 A1 | 10/1999 |
| WO | WO 99/59658 A1 | 11/1999 |
| WO | WO 00/07539 A1 | 2/2000 |
| WO | WO 00/13723 A2 | 3/2000 |
| WO | WO 00/24441 A1 | 5/2000 |
| WO | WO 00/35516 | 6/2000 |
| WO | WO 00/50107 A1 | 8/2000 |
| WO | WO 00/61209 A1 | 10/2000 |
| WO | WO 00/64515 A1 | 11/2000 |
| WO | WO 00/69488 A2 | 11/2000 |
| WO | WO 01/05456 A1 | 1/2001 |
| WO | WO 01/49347 A1 | 7/2001 |
| WO | WO 01/60435 A1 | 8/2001 |
| WO | WO 01/76666 A1 | 10/2001 |
| WO | WO 01/77384 A2 | 10/2001 |
| WO | WO 01/87384 A1 | 11/2001 |
| WO | WO 02/11799 A1 | 2/2002 |
| WO | WO 02/47746 A1 | 6/2002 |
| WO | WO 02/056947 A1 | 7/2002 |
| WO | WO 02/074361 A2 | 9/2002 |
| WO | WO 03/013632 A2 | 2/2003 |
| WO | WO 03/015846 A2 | 2/2003 |
| WO | WO 03/015853 A1 | 2/2003 |
| WO | WO 03/039633 A2 | 5/2003 |
| WO | WO 03/041768 A | 5/2003 |
| WO | WO 03/047663 A2 | 6/2003 |
| WO | WO 03/051434 A2 | 6/2003 |
| WO | WO 03/066141 A1 | 8/2003 |
| WO | WO 03/092771 | 11/2003 |
| WO | WO 03/097133 | 11/2003 |
| WO | WO 03/099358 A2 | 12/2003 |
| WO | WO 2004/007554 A1 | 1/2004 |
| WO | WO 2004/011065 A1 | 2/2004 |
| WO | WO 2004/030732 A2 | 4/2004 |
| WO | WO 2004/035117 A2 | 4/2004 |
| WO | WO 2004/047890 A1 | 6/2004 |
| WO | WO 2004/047891 A1 | 6/2004 |
| WO | WO 2004/047892 A | 6/2004 |
| WO | WO 2004/054644 A1 | 7/2004 |
| WO | WO 2004/054645 A3 | 7/2004 |
| WO | WO 2004/087242 A1 | 10/2004 |
| WO | WO 2004/101025 A2 | 11/2004 |
| WO | WO 2004/108194 A1 | 12/2004 |
| WO | WO 2005/004961 A1 | 1/2005 |
| WO | WO 2005/009515 A1 | 2/2005 |
| WO | WO 2005/023341 A1 | 3/2005 |
| WO | WO 2005/025636 A2 | 3/2005 |
| WO | WO 2005/030301 A1 | 4/2005 |
| WO | WO 2005/035028 A1 | 4/2005 |
| WO | WO 2005/044345 A | 5/2005 |
| WO | WO 2005/044347 A1 | 5/2005 |
| WO | WO 2005/058393 A2 | 6/2005 |
| WO | WO 2005/058396 A1 | 6/2005 |
| WO | WO 2005/070481 A1 | 8/2005 |
| WO | WO 2005/082438 A1 | 9/2005 |
| WO | WO 2005/097238 A3 | 10/2005 |
| WO | WO 2005/105014 A2 | 11/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/115516 A1 | 12/2005 |
| WO | WO 2005/120607 A2 | 12/2005 |
| WO | WO 2006/008086 A1 | 1/2006 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 | 6/2007 |
| WO | WO 2007/066152 A | 6/2007 |
| WO | WO 2007/122193 A1 | 11/2007 |
| WO | WO 2007/129324 A2 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/075033 A | 6/2008 |
| WO | WO 2008/093063 A2 | 8/2008 |
| WO | WO 88/08725 | 11/2008 |
| WO | WO 2010/023303 A1 | 3/2010 |
| WO | WO 2012/000835 A1 | 1/2012 |

OTHER PUBLICATIONS

International Search Report dated Sep. 5, 2005; International Application No. PCT/GB2005/002117.
International Search Report dated May 30, 2006; International Application No. PCT/GB2005/003725.
International Search Report dated Sep. 9, 2005; International Application No. PCT/GB2005/002126.
Australian Search Report dated Dec. 6, 2007; Application No. SG 200608164-0.
International Search Report dated Sep. 5, 2005; International Application No. PCT/GB2005/002131.
Austrian Search Report dated Jan. 22, 2006; Application No. 200608166-5.
International Search Report dated Sep. 9, 2005; International Application No. PCT/GB2005/002120.
International Search Report dated Sep. 6, 2005; International Application No. PCT/GB2005/002108.

(56) References Cited

OTHER PUBLICATIONS

European Search Report dated Apr. 23, 2007; Application No. 06077332.2.
International Search Report dated Sep. 5, 2005; International Application No. PCT/GB2005/002105.
Singapore Search Report dated Feb. 26, 2008; Application No. 200608070-9.
International Search Report dated Sep. 5, 2005; International Application No. PCT/GB2005/002116.
International Search Report dated Sep. 5, 2005; International Application No. PCT/GB2005/002128.
Australian Search Report dated Dec. 11, 2007; Application No. 200608165-7.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.
International Search Report dated Feb. 27, 2007; International Application No. PCT/IB2006/002792.
European Search Report dated Feb. 1, 2006; Application No. 05255298.1.
Great Britain Search Report dated Sep. 22, 2006; Application No. GB0610860.9.
International Search Report dated Aug. 22, 2007; International Application No. PCT/GB2007/001992.
International Search Report dated Sep. 4, 2007; International Application No. PCT/GB2007/002002.
Great Britain Search Report dated Sep. 28, 2006; Application No. GB0610859.1.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
Great Britain Search Report dated Nov. 12, 2007; Application No. GB0715460.2.
International Search Report dated Oct. 14, 2008; International Application No. PCT/GB2008/002580.
Great Britain Search Report dated Nov. 12, 2007; Application No. GB0715459.4.
International Search Report dated Nov. 27, 2008; International Application No. PCT/GB2008/002579.
Great Britain Search Report dated Nov. 12, 2007; Application No. GB0715461.0.
International Search Report dated Oct. 10, 2008; International Application No. PCT/GB2008/002573.
Great Britain Search Report dated Nov. 12, 2007; Application No. GB0715456.0.
International Search Report dated Oct. 10, 2008; International Application No. PCT/GB2008/002583.
Great Britain Search Report dated Nov. 12, 2007; Application No. GB0715457.8.
International Search Report dated Sep. 30, 2009; International Application No. PCT/GB2009/001447.
Great Britain Search Report dated Sep. 25, 2008; Application No. GB0811348.2.
International Search Report dated Oct. 2, 2009; International Application No. PCT/GB2009/001448.
Great Britain Search Report dated Sep. 25, 2008; Application No. GB0811346.6.
International Search Report dated Oct. 5, 2009; International Application No. PCT/GB2009/001451.
Great Britain Search Report dated Sep. 25, 2008; Application No. GB0811347.4.
International Search Report dated Oct. 6, 2009; International Application No. PCT/GB2009/001453.
Great Britain Search Report dated Sep. 25, 2008; Application No. GB0811345.8.
International Search Report dated Oct. 5, 2009; International Application No. PCT/GB2009/001445.
Great Britain Search Report dated Sep. 25, 2008; Application No. GB0811349.0.
International Search Report dated Jan. 22, 2010; International Application No. PCT/GB2009/001446.
Great Britain Search Report dated Sep. 25, 2008; Application No. GB0811343.3.
International Search Report dated Jan. 12, 2008; International Application No. PCT/GB2008/002475.
Great Britain Search Report dated Nov. 16, 2007; Application No. GB0716774.5.
European Search Report dated Aug. 3, 2011; Application No. 11163779.9.
Singapore Search Report dated Mar. 15, 2012; Application No. SG 201007017-5.
European Search Report dated Jul. 20, 2011; Application No. 11163762.5.
Australian Search Report dated Feb. 26, 2008; Application No. SG 200608071-7.
International Search Report dated Sep. 5, 2005; International Application No. PCT/GB2005/002137.
European Search Report dated Feb. 28, 2011; Application No. 10179733.0.
European Search Report dated Mar. 4, 2011; Application No. 10179736.3.
European Search Report dated Jun. 16, 2011; Application No. 11160134.0.
European Search Report dated Apr. 17, 2012; International Application No. 12157660.7.
European Search Report dated Apr. 17, 2012; International Application No. 12157661.5.
European Search Report Dated Oct. 16, 2012; International Application No. 12177505.0.
European Search Report dated Aug., 4, 2011; Application No. 11169691.0.
Great Britain Search Report dated Sep. 29, 2006; Application No. GB0610856.7.
Great Britain Search Report dated Sep. 19, 2006; Application No. GB0610861.7.
European Search Report dated Oct. 15, 2013; Application No. 12182553.3.
Great Britain Search Report dated Dec. 9, 2013; Application No. GB1310394.0.
Great Britain Search Report dated Dec. 8, 2013; Application No. GB1310389.0.
Great Britain Search Report dated Dec. 9, 2013; Application No. GB1310402.1.
Great Britain Search Report dated Dec. 9, 2013; Application No. GB1310392.4.
Great Britain Search Report dated Dec. 10, 2013; Application No. GB1310393.2.
Great Britain Search Report dated Dec. 10, 2013; Application No. GB1310372.6.
International Search Report dated Sep. 8, 2014; International Application No. PCT/EP2014/062163.
International Search Report dated Sep. 8, 2014; International Application No. PCT/EP2014/062166.

(56) References Cited

OTHER PUBLICATIONS

International Search Report dated Sep. 17, 2014; International Application No. PCT/EP2014/062167.
International Search Report dated Jan. 29, 2015; International Application No. PCT/EP2014/062167.
International Search Report dated Sep. 9, 2014; International Application No. PCT/EP2014/062168.
International Search Report dated Sep. 8, 2014; International Application No. PCT/EP2014/062162.
International Search Report dated Sep. 16, 2014; International Application No. PCT/EP2014/062160.
European Search Report dated Apr. 28, 2015; Application No. 15153304.9.
International Preliminary Report dated Dec. 15, 2015; International Application No. PCT/EP2014/062163.
International Preliminary Report dated Dec. 15, 2015; International Application No. PCT/EP2014/062166.

* cited by examiner

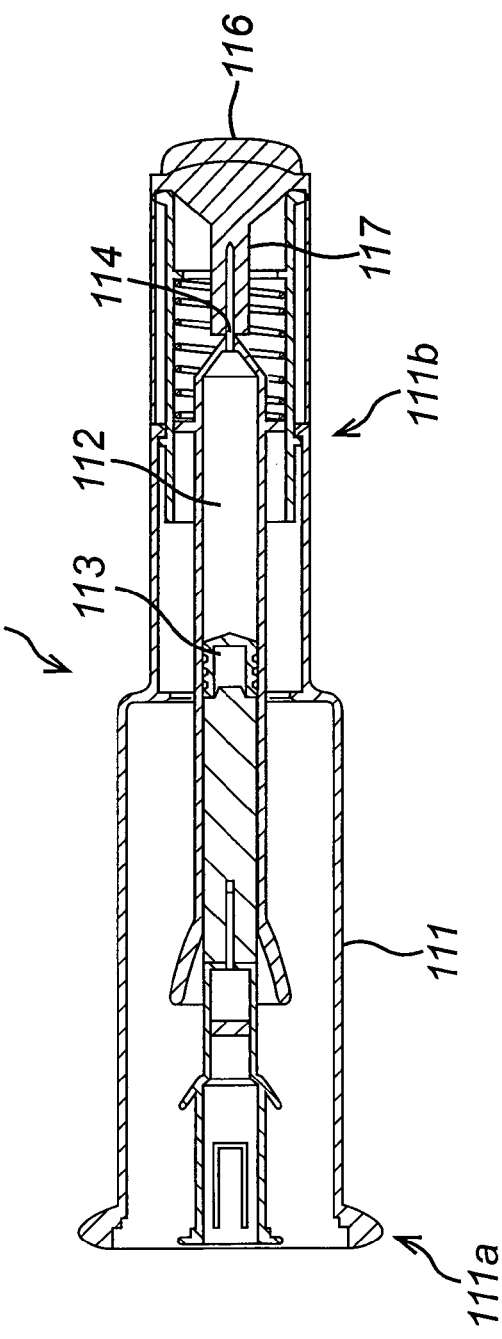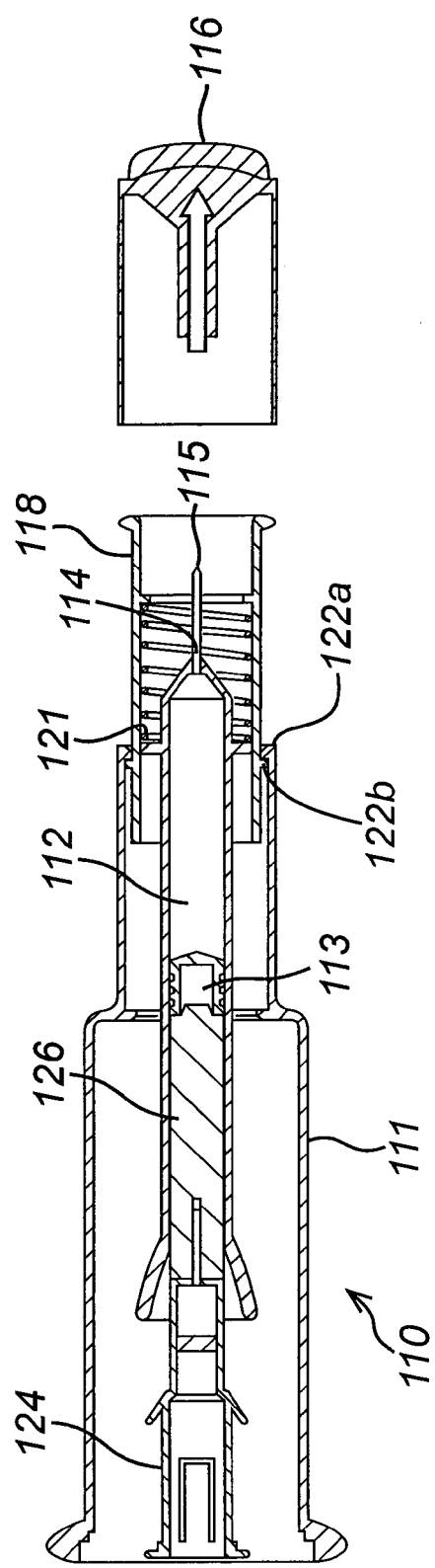

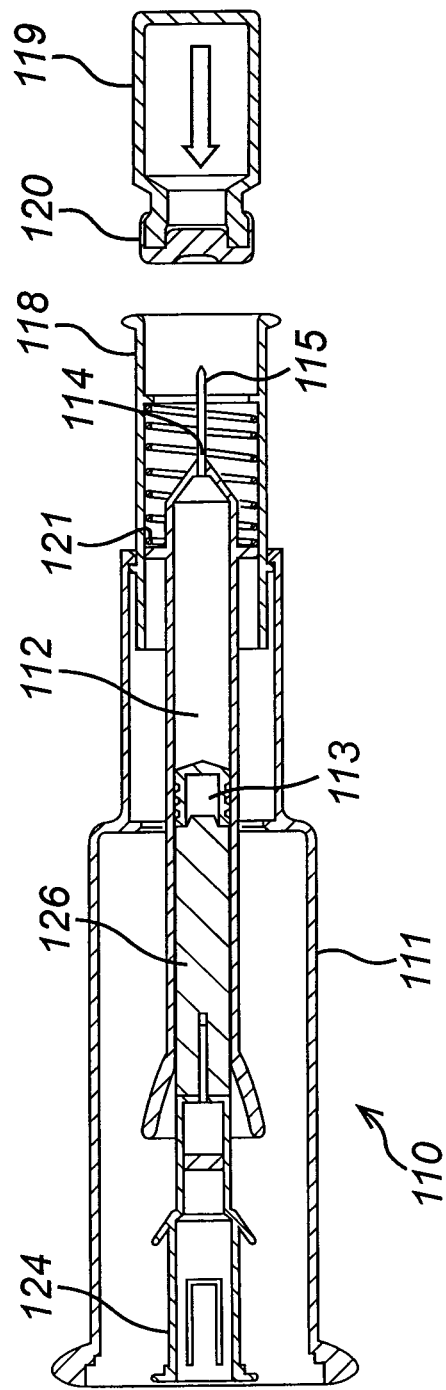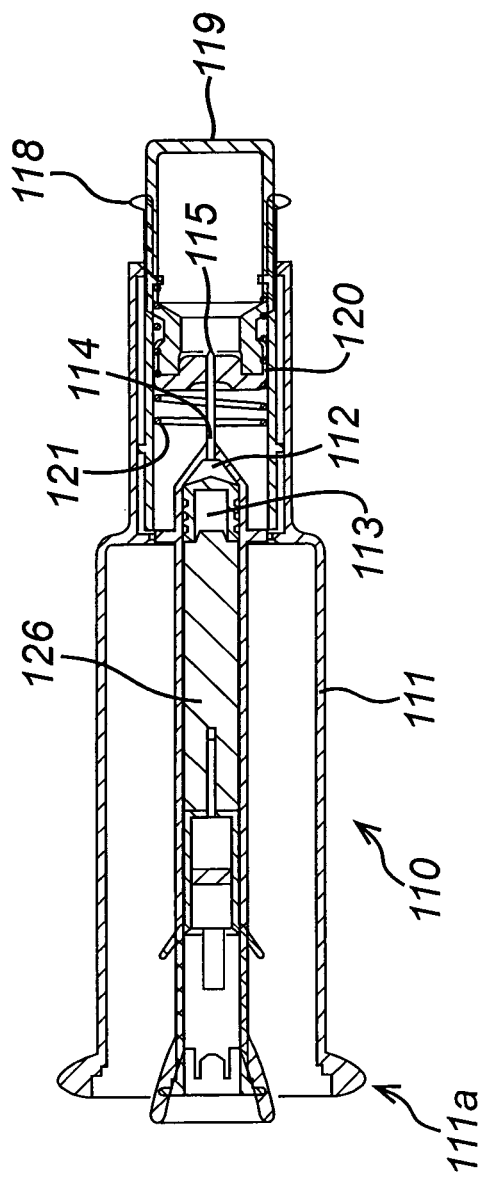

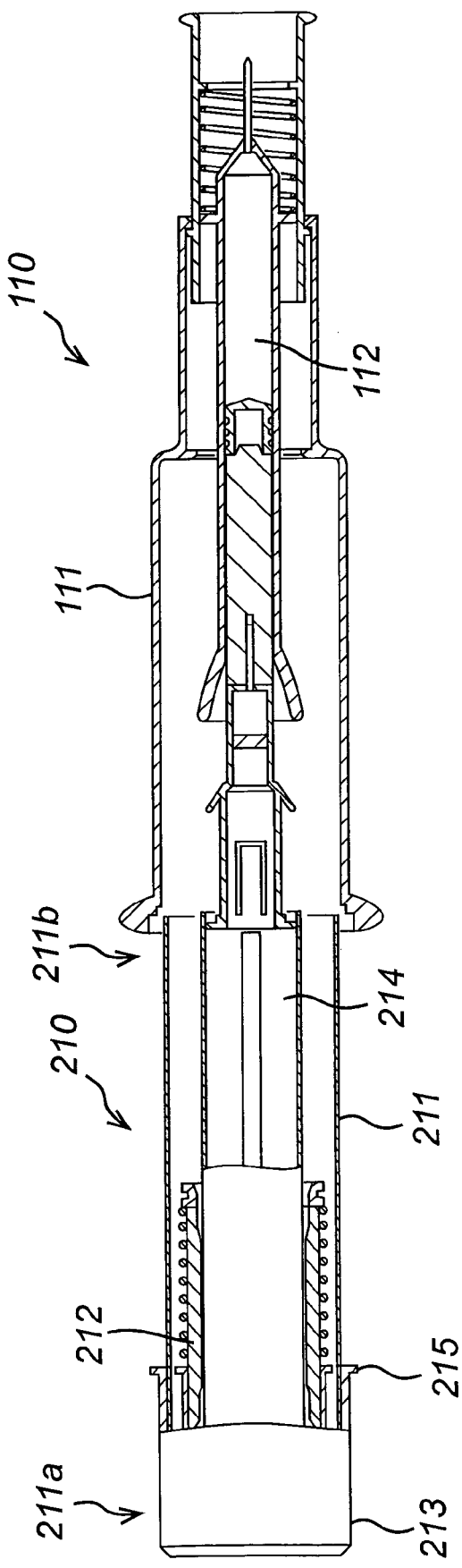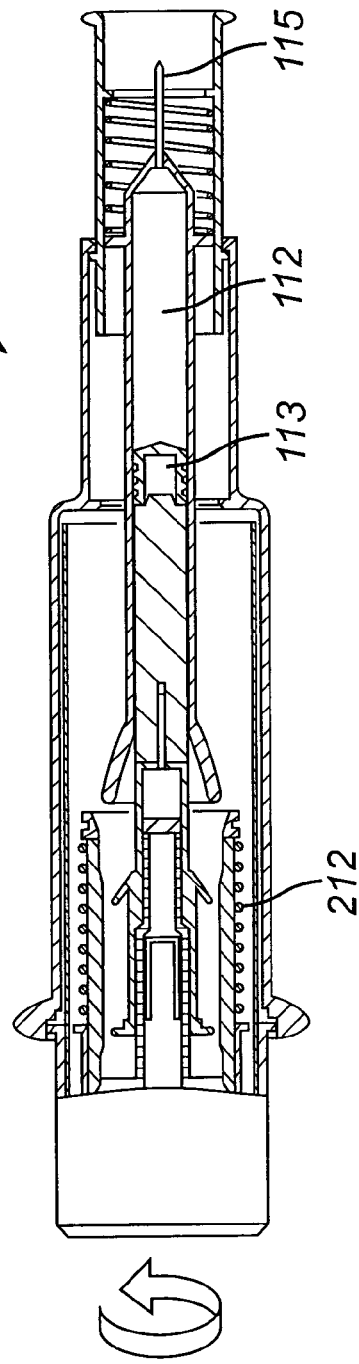

RE-USEABLE AUTO-INJECTOR WITH FILLING MEANS

FIELD OF THE INVENTION

This invention relates to an injection device, for example, a re-useable auto-injector into which a drug may be transferred from a vial prior to subcutaneous injection into a patient.

BACKGROUND OF THE INVENTION

The use of automatic injection devices (commonly known as auto-injectors) to deliver a medicament to a patient has provided many benefits over manual syringes. In particular, auto-injectors have helped to relieve the burden on hospital staff to deliver a drug to a patient because patients are able to use the devices on themselves reliably and safely and in their own home.

Known auto-injectors are described in WO 95/35126 and EP-A-0 516 473. These and similar auto-injectors are typically provided primed (i.e. pre-sprung) and ready to be used for injecting a patient. For these reasons, it is difficult to insert a drug into the auto-injector and, as a consequence, manufacturers of such auto-injectors have typically provided a pre-filled syringe for use in the auto-injector, or a complete auto-injector unit which is pre-filled with a particular drug.

This requires a more complicated and expensive manufacturing process than would be otherwise required for an auto-injector because manufacturers must also obtain and provide the drugs and maintain the facilities for storing and handling them. Furthermore, the manufacturer must operate separate production lines for each drug which is required.

Drugs for medical use are often manufactured and distributed in standard vials. In this way, drugs may be supplied in bulk conveniently and relatively cheaply, regardless of the way in which the drug is finally used.

A significant cost-saving could be made in providing an auto-injector device which is capable of drawing a drug from a standard vial rather than relying on a pre-filled syringe. Not only would such a device benefit the manufacturers, who would no longer have to provide bespoke drug-filled devices, but also hospitals, which would enjoy a simplified inventory system and could make use of the standard vials which are used on a regular basis, and patients, who could be provided with a supply of vials for self administration.

In addition, the use of vials permits the possibility of reusing a greater proportion of an auto-injector device. Typically, auto-injectors are provided in two subassemblies. The first subassembly comprises the operating mechanisms and all other reusable components and the second subassembly contains the injection components that must be replaced each time the device is used.

A major factor in the cost of the second subassembly is the provision of a chamber which is pre-filled with a drug to be injected. As explained above, providing a range of syringes is an expensive and time-consuming aspect of the manufacturing process of an auto-injector. The use of standard vials would enable this cost to be reduced.

SUMMARY OF THE INVENTION

The present invention aims to solve the aforementioned problems. Accordingly, an injection device comprises a housing; a chamber disposed within the housing, the chamber having proximal and distal ends, an inner surface and an exit aperture; a stopper movably disposed within the chamber, and having an outer surface substantially in contact with the inner surface about its perimeter; and a port adapted to receive a container containing a fluid. The stopper is fixed with respect to the housing and movement of the port causes movement of the exit aperture in relation to the stopper.

Providing an injection device, such as an auto-injector, having a chamber into which a fluid may be transferred from a separate container provides at least two benefits over the prior art. Firstly, manufacturers of auto-injector devices need no longer manufacture a range of pre-filled syringes to be inserted into a reusable sub-assembly. Rather, the manufacturer may provide instead a single type of sub-assembly in accordance with the present invention into which any variety of drug may be transferred immediately prior to injection. The single type of sub-assembly may be manufactured in bulk, thereby reducing the manufacturing costs.

This advantage leads on to a second benefit whereby the invention may be used in conjunction with any type of container from which a drug may be transferred into the chamber. In particular the invention may be used with standard vials.

Furthermore, the invention allows a greater proportion of the needle assembly to be reused. Whereas known auto-injector systems require pre-filled syringes, the capability of transferring fluid into a chamber within the needle device permits greater scope for reusability.

The volume of the chamber into which the fluid is transferred is defined by the space between the stopper and the exit aperture. Consequently, the volume is decreased as the stopper is moved toward the exit aperture and increased as the stopper is moved away from the exit aperture. An increase in volume causes an initial decrease in pressure in the chamber which thereby draws the fluid into the chamber.

The port may be configured to bring the container into fluid engagement with the exit aperture when the exit aperture is adjacent the stopper. In this position, the volume of the chamber is at or substantially at its lowest. Preferably, engagement between the container and the exit aperture forms a fluid conduit for transferring fluid from the container to the chamber. In accordance with this embodiment, as the volume of the chamber is increased (for example, by moving the exit aperture away from the stopper) fluid from the container is transferred into the chamber.

In some embodiments, a biasing element is coupled to the port and configured to bias the port such that the exit aperture is biased away from the stopper. Starting from the position mentioned above (i.e. wherein the exit aperture is adjacent the stopper and the container is in fluid engagement with the exit aperture), the action of the biasing element will cause the fluid to be transferred into the chamber without the need for external intervention. Optionally the biasing element is a spring, but other elements which perform a similar function are also envisaged.

In other embodiments, the injection device comprises a discharge nozzle in fluid communication with the exit aperture. Typically, containers suitable for use with the device comprise a cap made from rubber or foil, for example. In such cases, the discharge nozzle may be configured to pierce the cap to form a fluid conduit for transferring fluid from the container to the chamber.

BRIEF DESCRIPTION OF THE DRAWINGS

The invention will now be described by way of example with reference to the accompanying drawings, in which:

FIG. 1 is a side view of a first sub-assembly of an injection device;

FIG. 2 is a side view of the first sub-assembly wherein the cap has been removed;

FIG. 3 is a side view of a container being engaged with the first sub-assembly;

FIG. 4 is a side view of the first sub-assembly in the fully retracted position;

FIG. 7 is a side view of the first sub-assembly being engaged with a second sub-assembly; and FIG. 8 is a side view of an injection device comprised of the first and second sub-assemblies.

DETAILED DESCRIPTION OF THE DRAWINGS

Figure 5:
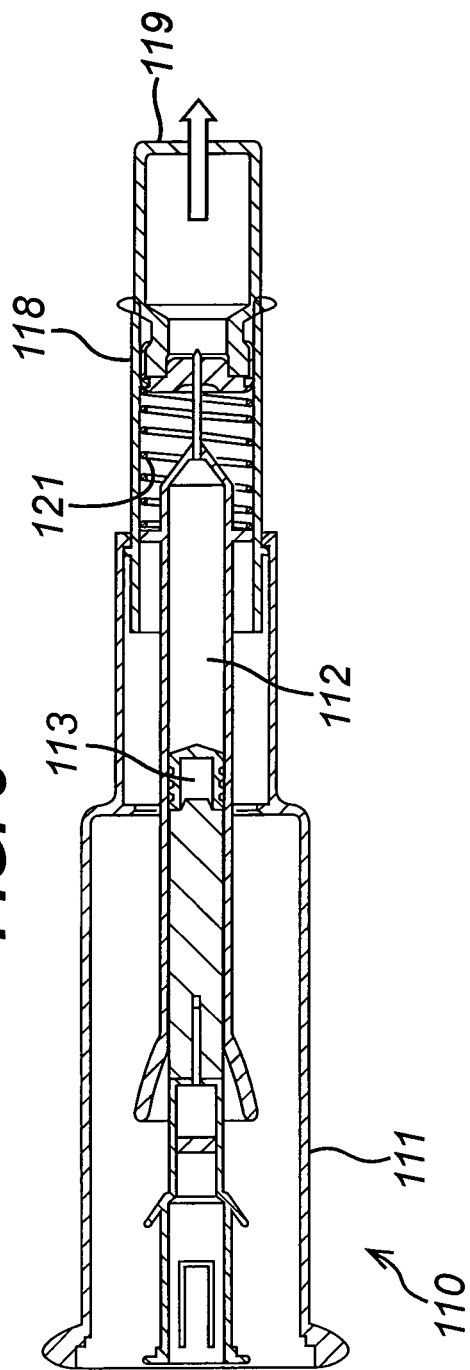
FIG. 5 is a side view of the first sub-assembly in the fully extended position.

FIGS. 1 to 4 illustrate a first sub-assembly 110 suitable for use in an auto-injector according to the present invention.

The first sub-assembly 110 comprises a housing 111 and a chamber 112 disposed within the housing. The housing 111 has proximal 111a and distal 111b ends. The chamber 112 has proximal and distal ends, corresponding to the proximal and distal ends of the housing, and an inner surface. Adjacent the proximal end of the chamber there is provided a stopper 113. The stopper 113 is moveably disposed within the chamber 112 and has an outer surface. The outer surface of the stopper 113 is substantially in contact with the inner surface of the chamber 112 about its perimeter.

At the distal end of the chamber 112 there is provided an exit aperture 114. An injection needle 115 is provided in fluid connection with the exit aperture 114. The injection needle 115 is suitable for piercing the skin of a patient and delivering a drug subcutaneously. The needle 115 is also suitable for piercing a foil or rubber cap as might be provided on a vial.

The first sub-assembly 110 comprises a removable cap 116 including a sheath 117 disposed over the needle 115. The sheath 117 protects the needle and provides a substantially fluid tight seal over the tip of the needle, to prevent unwanted fluid ingress or egress.

FIG. 2 illustrates the first sub-assembly of FIG. 1 wherein the cap 116 has been removed from the first sub-assembly 110. In removing the cap 116, the sheath 117 has been removed from the needle 115. As can be seen in this figure, the first sub-assembly comprises a port 118 (or sleeve). In this configuration, the port 118 surrounds the needle to prevent damage to the needle or accidental contact between the needle and the user.

The port 118 is moveable in relation to the housing 111 but is coupled to the chamber 112 such that movement of the port 118 causes a corresponding movement of the chamber 112 and the exit aperture 114, relative to the housing 111. In FIG. 2, the port 118, and hence the chamber 112, are in a fully extended position.

The sub-assembly 110 comprises a biasing element 121 which acts on the port 118 to bias it away from the housing 111. In so doing, the biasing element 121 biases the exit aperture 114 of the chamber 112, which is moveable in relation to the housing 111, away from the stopper 113 which, at this point in the operation of the auto-injector (i.e. prior to activation of the auto-injector; specifically prior to advancement of the needle assembly out of the housing) is fixed in relation to the housing. As shown in FIG. 2, the stopper 113 is coupled to a support rod 124 via a support block 126. The support rod is attached to the housing 111. The stopper 113 abuts the support block 126 and remains stationary with respect to the support rod 124 when the port 118 and the chamber 112 are advanced toward the proximal end 111a of the housing (described in detail below). The chamber is configured to slide over the support rod 124 and support block 126.

At its distal end 111a, the housing 111 comprising a first detent 122a. A second detent 122b, provided on the port 118, interfaces with the first detent 122a when the port 118 and the chamber 112 are in a fully extended position. The detents 122 prevent the port 118 from being extended beyond this position by action of the biasing element 121.

As shown in FIG. 3, the port 118 is adapted to receive a container 119 containing a fluid, for example a pharmaceutical product. FIG. 3 depicts a vial, but other containers may be used. The container 119 includes a cap 120 at one end. As illustrated, the end of the container having the cap 120 is inserted into the port 118 whilst the port is in an extended position. The port 118 is sized and shaped to accept the container 119 and hold it within the port 118 without the need for any additional locking mechanism. Of course, locking means may be provided to give better securement.

The available volume of the chamber 112 into which a fluid may be transferred depends on the distance between the stopper 113 and the exit aperture 114. In FIGS. 1 to 3, the available volume of the chamber 112 is substantially at its greatest. However, in this state, prior to the engagement of the container 119, the chamber 112 is empty. The process of transferring fluid from the container 119 to the chamber 112 will be described with reference to FIGS. 4 and 5.

As a user inserts the container 119 into the port 118, the container is retained inside the port by a flange (not shown) provided around the inner surface of the port 118. The flange occupies a recess in the container 119, thereby securing the container within the port 118.

As the container 119 is advanced further, the port 118 and the chamber 112 are driven towards the proximal end 111a of the housing 111. As the chamber 112 is moved towards the proximal end 111a of the housing, the exit aperture 114 is moved toward the stopper 113. The available volume of the chamber 112 decreases accordingly.

FIG. 4 shows the first sub-assembly 110 when the port 118 and the chamber 112 are in a fully retracted position. As illustrated, in the fully retracted position, the stopper 113 is immediately adjacent the exit aperture 114. In this configuration, the available volume of the chamber 112 is substantially at its lowest.

As the user engages the container 119 with the port 118, the injection needle 115 pierces the cap 120 and provides a fluid conduit between the container 119 and the chamber 112.

The fluid conduit begins at the container 119, passes through the injection needle 115 and the exit aperture 114 and ends at the chamber 112.

In FIG. 4, the fluid is contained within the container 119. As the user releases the container 119, the biasing element 121 forces the port 118 away from the housing 111 and, accordingly, forces the exit aperture 114 away from the stopper 113. The container 119 remains secured within the port 118 and engaged with the needle 115 which is moved along with the exit aperture 114. Thus, the fluid conduit is preserved.

As the exit aperture 114 moves away from the stopper 113, the available volume of the chamber 112 increases. The increase in volume of the chamber 112 causes a reduction in chamber pressure and the pressure difference between the vial and the chamber causes fluid to be drawn from the container 119 along the fluid conduit into the chamber 112. The further the exit aperture 114 moves away from the stopper 113, the more fluid is drawn into the chamber 112.

FIG. 5 illustrates the sub-assembly 110 after the biasing element 121 has forced the port 118 and the chamber 112 into the fully extended position. As before, the detents 122a,b on the housing 111 and the port 118 prevent the port 118 from being over extended. As shown, the fluid has been completely transferred from the container 119 to the chamber 112. The available volume of the chamber 112, between the stopper 113 and the exit aperture 114, is now filled with the fluid.

Figure 6:
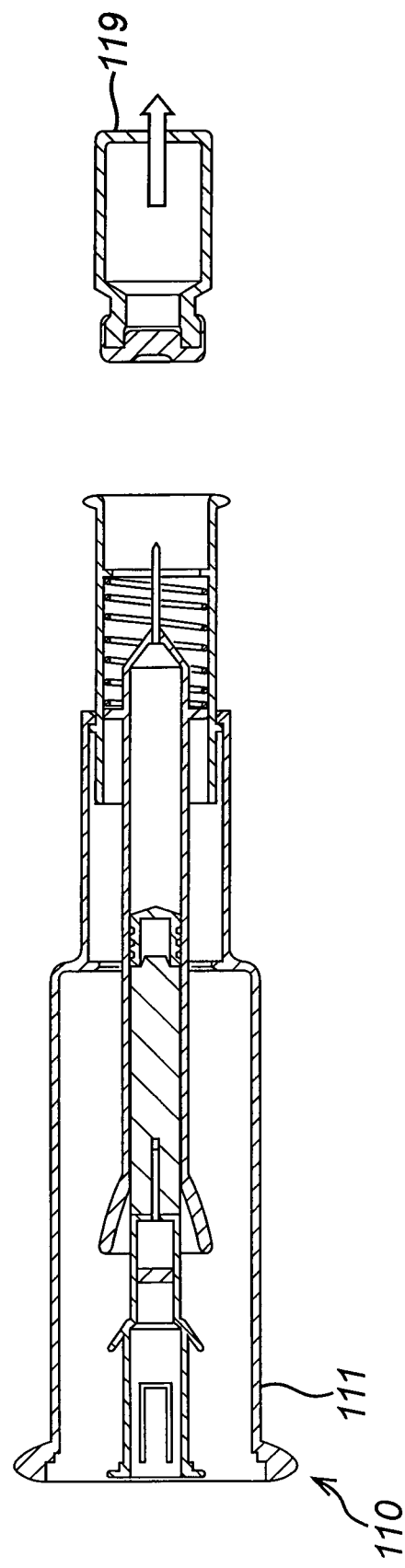
FIG. 6 is a side view of the container being removed from the first sub-assembly.

As it is now spent, the empty container 119 may be removed from the first sub-assembly 110 and discarded. FIG. 6 illustrates the first sub-assembly 110 which has been primed (i.e. filled with the fluid) and is ready to be used.

To administer the fluid, the first sub-assembly 110 is engaged with a second sub-assembly 210. As illustrated in FIG. 7, the second sub-assembly comprises a housing 211 and a drive mechanism 212. The housing has proximal 211a and distal 211b ends and a cap 213 located at the proximal end 211b. The cap includes a lip 215 which is engageable with the housing 111 of the first sub-assembly 110. A slot 214 is provided in the second sub-assembly 210.

Once the first sub-assembly 110 has been primed, the distal end 211b of the housing 211 of the second sub-assembly 210 is inserted into the proximal end 111a of the housing 111 of the first sub-assembly 110. The chamber 112 fits within the slot 214 and is coupled to the driving mechanism 212. The second sub-assembly 210 is secured to the first sub-assembly 110 by rotating the cap 213 which engages the lip 215 with the housing 111 of the first sub-assembly 110.

FIG. 8 illustrates an injection device 300 which has been primed and is ready to use. Activation of a firing mechanism of the injection device 300 actuates the driving mechanism 212 which exposes the needle 115 outside of the injection device 300 to pierce the skin of a patient and drives the stopper 113 through the chamber 112 to inject the patient with the fluid. The drive mechanism 212 subsequently retracts the needle 115 so that it is wholly within the injection device 300.

Once the fluid has been injected, the second sub-assembly 210 may be disassembled from the first sub-assembly 110 and reused. The first sub-assembly 110 may be discarded and a new first sub-assembly provided for subsequent injections, or may be sterilised for reuse.

It will be appreciated that modifications may be made to the embodiment described without departing from the scope of the invention, as defined in the appended claims.

The invention claimed is:

1. An injection device having a first sub-assembly, the first sub-assembly comprising:
    a housing;
    a chamber disposed within the housing and having proximal and distal ends, an inner surface and an exit aperture;
    a stopper movably disposed within the chamber and having an outer surface substantially in contact with the inner surface about its perimeter; and
    a port movable in relation to the housing and coupled to the chamber such that movement of the port causes a corresponding movement of the chamber and the exit aperture, relative to the housing, the port adapted to receive a container containing a fluid;
    wherein when the port and the chamber are moved in relation to the housing, the stopper remains stationary with respect to the housing such that movement of the port causes movement of the exit aperture in relation to the stopper, wherein the port is configured to bring said container into fluid engagement with the exit aperture when the exit aperture is adjacent the stopper.

2. The injection device of claim 1, further comprising an injection needle in fluid communication with the exit aperture.

3. The injection device of claim 2, wherein the container comprises a cap, and wherein the injection needle is configured to pierce the cap to form a fluid conduit for transferring fluid from the container to the chamber.

4. The injection device of claim 3 further comprising a second sub-assembly, the second sub-assembly comprising:
    a releasable drive mechanism configured to be driven against the stopper upon activation of the drive mechanism.

5. The injection device of claim 4, wherein the releasable drive mechanism is, upon activation, adapted to:
    (a) move the chamber and the injection needle from a retracted position in which the needle is wholly inside the housing to an extended position in which the needle is at least partially outside the housing; and
    (b) subsequently move the stopper within the chamber toward the exit aperture to expel fluid out of the injection needle.

6. The injection device of claim 5, further comprising a retraction mechanism adapted to retract the injection needle into the housing after the fluid has been expelled.

7. The injection device of any one of claims 4 to 6, wherein:
    the first sub-assembly is detachable from the second sub-assembly; and
    the second sub-assembly is reusable.

8. The injection device of claim 1, further comprising:
    a biasing element coupled to the port and configured to bias the port such that the exit aperture is biased away from the stopper.

9. The injection device of claim 1, wherein engagement between the container and the exit aperture forms a fluid conduit for transferring fluid from the container to the chamber.

10. A method of priming an injection device having a first sub-assembly comprising a housing, the method comprising the steps of:
    inserting a container into a port on the injection device, the port being moveable with respect to the housing, the first sub-assembly comprising a chamber having an exit aperture and a stopper movably disposed within the chamber, the chamber being coupled to the port such that movement of the port causes a corresponding movement of the chamber and the exit aperture, relative to the housing, wherein when the port and the chamber are moved in relation to the housing, the stopper remains stationary with respect to the housing such that movement of the port causes movement of the exit aperture relative to the stopper;
    moving the port into the housing; and
    moving the port out of the housing such that fluid is drawn into the chamber from the container.

\* \* \* \* \*